United States Patent
Harari et al.

(10) Patent No.: US 8,764,773 B2
(45) Date of Patent: Jul. 1, 2014

(54) SURGICAL PORT FOR NOTES PROCEDURES

(75) Inventors: Boaz Harari, Tel Aviv (IL); Leonid Monassevitch, Hadera (IL); Kobby Greenberg, Even Yehuda (IL)

(73) Assignee: Novogi Ltd., Netanya (IL)

(*) Notice: Subject to any disclaimer, the term of this patent is extended or adjusted under 35 U.S.C. 154(b) by 717 days.

(21) Appl. No.: 12/937,285

(22) PCT Filed: Apr. 7, 2009

(86) PCT No.: PCT/IL2009/000396
§ 371 (c)(1),
(2), (4) Date: Oct. 11, 2010

(87) PCT Pub. No.: WO2009/125403
PCT Pub. Date: Oct. 15, 2009

(65) Prior Publication Data
US 2011/0034767 A1 Feb. 10, 2011

Related U.S. Application Data

(60) Provisional application No. 61/071,023, filed on Apr. 9, 2008.

(51) Int. Cl.
*A61B 17/03* (2006.01)

(52) U.S. Cl.
USPC .......................................................... 606/151

(58) Field of Classification Search
CPC .. A61B 17/122; A61B 17/3423; A61B 17/08; A61B 2017/00278; A61B 2017/3425; A61B 2017/3427
USPC ................... 606/151–157, 219, 221; 600/218
See application file for complete search history.

(56) References Cited

U.S. PATENT DOCUMENTS

| 5,002,552 A | 3/1991 | Casey |
| 5,392,766 A | 2/1995 | Masterson |

(Continued)

FOREIGN PATENT DOCUMENTS

WO 2009/125403 A2 10/2009

OTHER PUBLICATIONS

International Search Report mailed Sep. 15, 2009 for PCT/IL09/00396 filed Apr. 7, 2009.

(Continued)

*Primary Examiner* — Julian W Woo
*Assistant Examiner* — Shaun L David
(74) *Attorney, Agent, or Firm* — Roach Brown McCarthy & Gruber, P.C.; Kevin D. McCarthy

(57) ABSTRACT

A dual use compression clip and surgical port device where the device serves as a surgical compression clip and surgical port in surgical procedures. The device comprises two compression elements each constructed having a bounding surface which when taken together form the boundary of a surgical port and one or more hinge elements in mechanical communication with the compression elements allowing the compression elements and the device to move from an open arrangement to a closed arrangement. The device also includes one or more apertures on each of the compression elements sized and configured to receive the insertion elements of an applicator instrument so that a force applied by the applicator instrument brings the device and compression elements from their open arrangement to their closed arrangement. A system and method for use of the device is also discussed.

9 Claims, 14 Drawing Sheets

(56) References Cited

U.S. PATENT DOCUMENTS

| | | |
|---|---|---|
| 5,676,674 A | 10/1997 | Bolanos |
| 6,428,548 B1 | 8/2002 | Durgin et al. |
| 2004/0054353 A1* | 3/2004 | Taylor ............................... 606/1 |
| 2005/0192596 A1* | 9/2005 | Jugenheimer et al. ........ 606/142 |
| 2005/0251204 A1* | 11/2005 | Attinger et al. ............... 606/221 |
| 2006/0241651 A1 | 10/2006 | Wilk |
| 2007/0213747 A1 | 9/2007 | Monassevitch et al. |

OTHER PUBLICATIONS

Written Opinion mailed Sep. 15, 2009 for PCT/IL09/00396 filed Apr. 7, 2009.

International Preliminary Search Report mailed Oct. 12, 2010 for PCT/IL09/00396 filed Apr. 7, 2009.

* cited by examiner

SURGICAL PORT FOR NOTES PROCEDURES

FIELD OF THE INVENTION

The present invention relates to the field of surgical ports and clips.

BACKGROUND OF THE INVENTION

Natural orifice transluminal endoscopic surgery (NOTES), which obviates the need for cutting through the abdominal wall, is a new and promising surgical technique. In NOTES, an incision is made from within a natural orifice, for example the gastrointestinal (GI) tract or other body lumen, to reach the peritoneal cavity or other organs. It is believed that NOTES will provide less invasive surgery reducing recovery time. It is also believed that the new procedure will generate less discomfort in the patient with fewer incisional complications including pain, hernias, and external wound infections. There should also be potentially fewer adhesions and a decreased need for anesthesia when NOTES is used. Hospital stays should also be shorter with a concomitant reduction in nosocomial infections. There should be virtually no visible scarring resulting from a NOTES procedure.

Closing perforations and openings after iatrogenic procedures, including NOTES procedures, requires wound closing instruments, systems and methods to prevent leakage into the peritoneal cavity or other body organs. At a recent meeting of a group of surgeons from the Society of American Gastrointestinal and Endoscopic Surgeons (SAGES) and gastroenterologists from the American Society of Gastrointestinal Endoscopists (ASGE), a framework for the initial safe application of NOTES procedures was discussed and worked out. It was agreed that further expansion of the use of NOTES procedures depends inter alia on an effective collaboration with industry. Development of effective instruments allowing traction/countertraction and stable optical platforms, as well as the means to control hemostasis, prevent infection, securely close the visceral wall, and perform suturing functions and gastrointestinal anastomoses were deemed critical.

Therefore, the development of new surgical ports and compression clips for use in NOTES and other surgical procedures is desirable.

SUMMARY OF THE INVENTION

It is an object of the present invention to provide a dual use compression clip and surgical port device for use in natural orifice transmural endoscopic surgery (NOTES) and other surgical procedures. It is a further object to provide a dual use compression clip and surgical port device which, in addition to serving as a compression clip, serves as a surgical port in such procedures, minimizing infection. It is yet a further object of the present invention to provide a system and method for using such a device.

It is an object of the present invention to provide a dual use compression clip and surgical port device which when functioning as a compression clip exerts a substantially constant, or slowly changing, compressive force irrespective of the thickness of the tissue being compressed, and irrespective of changes in tissue thickness during the wound healing process. Such a clip reduces the chances of liquid leakage during compression, ensures necrosis in an aseptic environment, and also provides for faster healing and closure of the tissue around an opening or other type of lesion.

It is a further object of the present invention to provide a dual use compression clip and surgical port device which is not left within the body after tissue closure is complete.

In one aspect of the present invention, there is provided a dual-use compression clip and surgical port device having an open and a closed position and which is removably attachable to an applicator instrument having insertion elements. The device includes: two compression elements, each element having formed thereon a bounding surface, the bounding surfaces being mutually complementary so as to combine to form the boundary of an opening when the device is in the open position; one or more hinge elements for connecting the two compression elements to each other for allowing the compression elements to move from an open arrangement corresponding to the open position to a closed arrangement corresponding to the closed position and vice versa; one or more force applier elements which have a first position when the device is in its open position wherein the one or more force applier elements are biased to apply a force to keep the compression elements in their open arrangement and suitable for use as a surgical port, the one or more force applier elements being selectably operable to apply to the compression elements a closure force and to maintain them in their closed arrangement when the compression elements have been brought to their closed arrangement and to maintain them in the closed arrangement; and one or more engageable surface features formed on each of the compression elements sized and configured to receive the insertion elements of the applicator instrument so that a force provided by the applicator instrument brings the compression elements from the open arrangement to the closed arrangement, thereby allowing the device to function as a compression clip when in its closed position.

In some embodiments, the device further includes an elastomeric membrane covering the opening of the device. The membrane in some instances includes a slit for passing working tools required for a surgical procedure through the membrane.

In another embodiment, the one or more force applier elements are formed of a shape memory alloy.

In another embodiment of the device, each of the two compression elements of the device includes a lip. In the lip of one of the two compression elements are embedded a plurality of staples while in the lip of the second of the two compression elements are positioned a plurality of anvil recesses. The recesses are positioned to be in registration with the staples. When the compression elements are brought to their closed arrangement and under a force produced by the one or more force applier elements, the staples are crimped in the anvil recesses after passing through tissue held between the two compression elements.

In a second aspect of the invention, there is provided a system for use as a dual use compression clip and surgical port, the system comprising a dual-use compression clip and surgical port device and one or more anchoring elements to anchor the device adjacent to tissue selected to undergo a surgical procedure. The device has an open and a closed position and is removably attachable to an applicator instrument having insertion elements. The device includes two compression elements, each element having formed thereon a bounding surface, the bounding surfaces being mutually complementary so as to combine to form the boundary of an opening when the device is in the open position; one or more hinge elements for connecting the two compression elements to each other for allowing the compression elements to move from an open arrangement corresponding to the open position to a closed arrangement corresponding to the closed position and vice versa; one or more force applier elements which have a first position when the device is in its open position wherein the one or more force applier elements are biased to apply a force to keep the compression elements in their open arrangement and suitable for use as a surgical port, the one or more force applier elements being selectably operable to apply to the compression elements a closure force and to maintain them in the closed arrangement when so as to bring the compression elements have been brought to their closed arrangement and to maintain them in the closed arrangement; and one or more engageable surface features formed on each of the compression elements sized and configured to receive the insertion elements of the applicator instrument so that a force provided by the applicator instrument brings the compression elements from the open arrangement to the closed arrangement, thereby allowing the device to function as a compression clip when in its closed position, and one or more anchoring means for anchoring the device to tissue adjacent to, or within an operational distance of, an organ selected to undergo a surgical procedure.

In one embodiment of the system, the device further includes an elastomeric membrane covering the opening of the device.

In another embodiment of the system, the one or more force applier elements are formed of a shape memory alloy.

In yet another embodiment of the system, the system further includes a hollow placement means removably attachable to the device for delivering the device to tissue adjacent to, or within an operational distance of, the organ selected to undergo the surgical procedure.

In still another embodiment of the system, the hollow placement means is also usable for inserting therethrough an endoscope and working surgical instruments and for delivering them to the device.

In yet another aspect of the invention, there is provided a method of localized surgical compression using a dual-use compression clip and surgical port device having complementary halves and an open and a closed position, the method comprising the steps of:

bringing the device to tissue adjacent to, or within an operational distance of, an organ selected to undergo a surgical procedure;

anchoring the device to the tissue adjacent to, or within an operational distance of, the organ;

conveying an endoscope, and ancillary working surgical instruments therein, to the device;

passing the endoscope and ancillary working surgical instruments through an opening formed by the complementary halves of the device in its open position to effect the surgical procedure on the organ and then withdrawing the endoscope and the ancillary instruments through the opening after completion of the procedure; and attaching an applicator instrument to the device and then using the applicator instrument to apply a force to bring the complementary halves of the device together so that they compress tissue located therebetween.

In an embodiment of the method, the method further includes the step of attaching a hollow placement means to the device, the hollow placement means operable for placement of the device in the step of bringing. In instances of this embodiment the step of attaching is effected with the device in its open position.

In another embodiment of the method, the step of anchoring includes stapling a membrane positioned between the complementary halves of the device to tissue adjacent to, or within an operational distance of, the organ selected to undergo the surgical procedure.

In still another embodiment of the method where a membrane is present, the method includes a step of cutting the membrane positioned between the complementary halves of the device to allow the endoscope, and working surgical instruments therein, to pass through the membrane and to approach the tissue adjacent to, or within an operational distance of, the organ selected to undergo the surgical procedure.

In yet another embodiment of the method, the method is used in a NOTES procedure and the method further includes a step of cutting through the tissue of a wall of a body lumen to which the device has been brought in the step of bringing and anchored in the step of anchoring, thereby to allow the endoscope and working surgical instruments in the step of passing to approach and operate on the organ selected to undergo the surgical procedure, the organ located outside the body lumen.

The method may be used with any of the embodiments of the device described above.

DEFINITIONS

"Proximal" relates to the side of the device closest to the user, while "distal" refers to the side of the device furthest from the user.

"Top side"—refers to the side of the open device furthest from the tissue being treated. This is the side of the open device wherein the engageable surface features for receiving the insertion elements of an applicator instrument, as discussed herein, are located.

"Bottom side"—refers to the side of the open device closest to the tissue being treated.

"Gastrointestinal tract" or its equivalents are used in the specification and claims, without any intent at being limiting. Other organ systems, and lesions found therein, are also contemplated as being treatable with the devices, systems and methods described in the present specification.

"Spring" or "leaf spring" are to be construed as being specific types of "force applier elements". This latter term may be used herein interchangeably with spring or leaf spring without any intent at differentiating between these terms, except where specifically indicated. Elements having other shapes may also be used as force appliers if their operation and function are essentially similar to that of the spring and leaf spring discussed herein. Force appliers may be made of shape-memory materials, as well as other materials, such as conventional metallic spring materials, or elastomers, such as rubbers.

BRIEF DESCRIPTION OF THE DRAWINGS

The present invention will be more fully understood and its features and advantages will become apparent to those skilled in the art by reference to the ensuing description, taken in conjunction with the accompanying drawings, in which.

Similar elements in the Figures are numbered with similar reference numerals.

DETAILED DESCRIPTION OF THE PREFERRED EMBODIMENTS

Figure 1A:
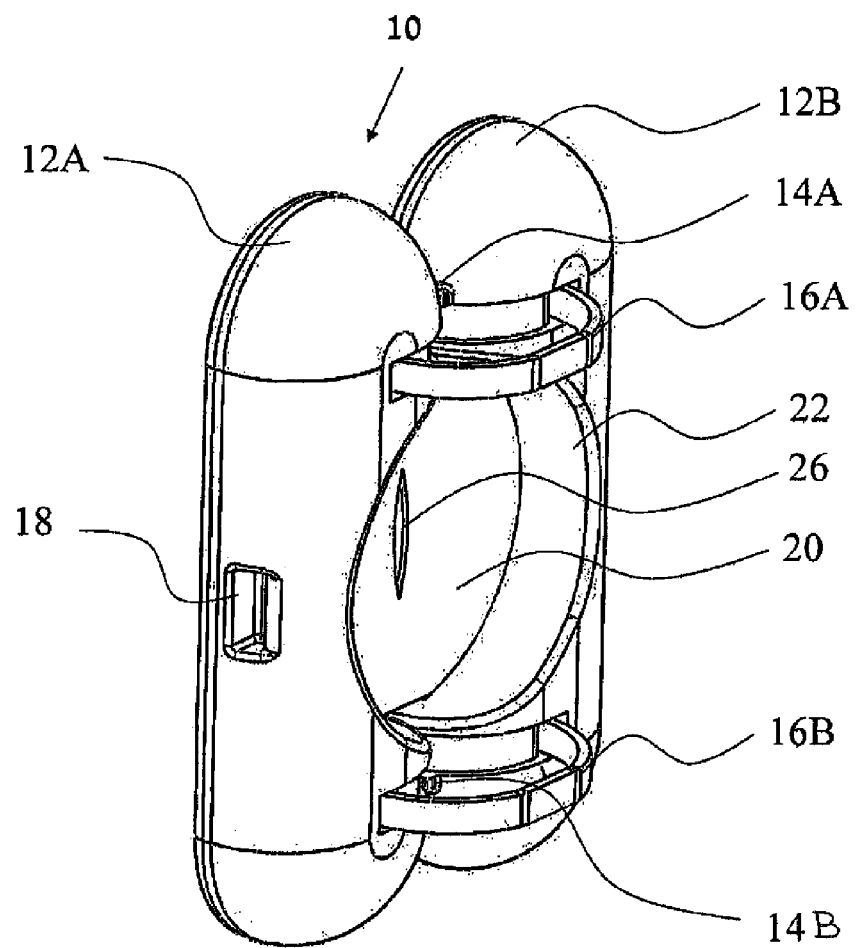
FIG. 1A is an isometric view of an open dual use compression clip and surgical port device for use inter alia in NOTES procedures, the device constructed according to an embodiment of the present invention and viewed from its top side.

The present invention describes a dual use compression clip and surgical port device (herein often referred to as the "device") for use in surgical procedures, including NOTES procedures, which is suitable for use as a surgical port and compression clip in such procedures. A system and method for using such devices are also described.

The non-unitary, i.e. compound, surgical device described herein, typically has one or more force applier elements, generally two or more force applier elements, made of a shape-memory material, such as a nickel-titanium (Ni—Ti) alloy. The device includes two compression elements hingeably connected and operationally held open in a first arrangement or closed in a second arrangement by at least one of the shape-memory elements. Typically, the device is also secured to tissue being compressed. The compression elements are formed so that in their open first arrangement they are constructed so as to form and serve as a surgical port in a NOTES procedure. When tissue to be joined is held between the two compression elements, a substantially constant or slowly changing compressive force acts between the two elements. The compression elements are held in a compressive state by the shape-memory force applier elements. The slowly changing force is a result of the long plateau region of the shape-memory material's stress-strain hysteresis curve. The force is slowly changing irrespective of deformation in the deformation range of the plateau. The shape-memory elements, which act as a force applier, are typically made of nickel-titanium (Ni—Ti) alloys but other shape memory materials may also be used. Stress-induced strain is recoverable in these materials; in the case of Ni—Ti alloys, 6-8% of the strain can be recovered.

In some embodiments of the present invention, the force applier elements may be constructed of materials other than shape-memory materials. These materials may be other resilient materials such as elastomers, for example rubbers, or metals used in constructing conventional springs.

The surgical devices described herein may be used with standard commercially available endoscopes. Dedicated or specially designed endoscopes may be used but are not required.

Current clips which are delivered to a treatment site using an endoscope or other medical instrument are typically limited in size. It is envisioned that the size of the device described herein which serves both as a surgical port and as a compression clip will allow closure of the relatively large tissue openings occurring in NOTES procedures. Similarly, the devices of the present invention described herein are able to close tissue openings in organs with relatively thick tissue such as that of the stomach.

Additionally, using the devices of the present invention is not limited to any particular direction or shape of incision; both radial and longitudinal incisions are contemplated by the present invention.

Before explaining embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The discussion below, with respect to the Figures presented herein, will be in terms of a NOTES procedure through the stomach wall and into the peritoneal cavity. It should be apparent that the devices discussed and the systems and method for their use can be used on NOTES procedures of other organs as well, such as, but without intending to limit the invention, the uterus, the large and small bowels, the rectum, and the urinary bladder. It should also be readily understood that the devices, systems and method of the present invention may be used for other types of surgical procedures in addition to NOTES procedures.

Figure 1B:
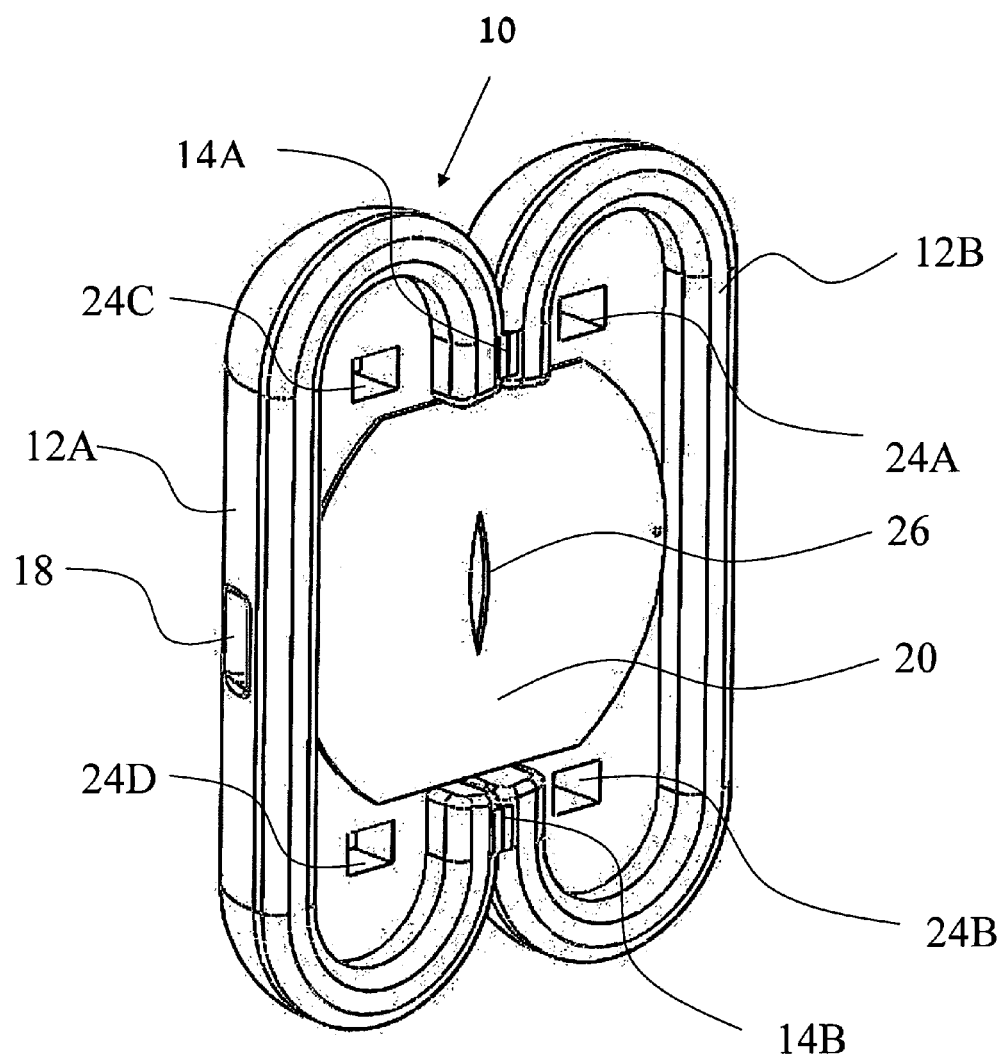
FIG. 1B is an isometric view of an open dual use compression clip and surgical port device for use inter alia in NOTES procedures, the device constructed according to an embodiment of the present invention and viewed from its bottom side.
Figure 1C:
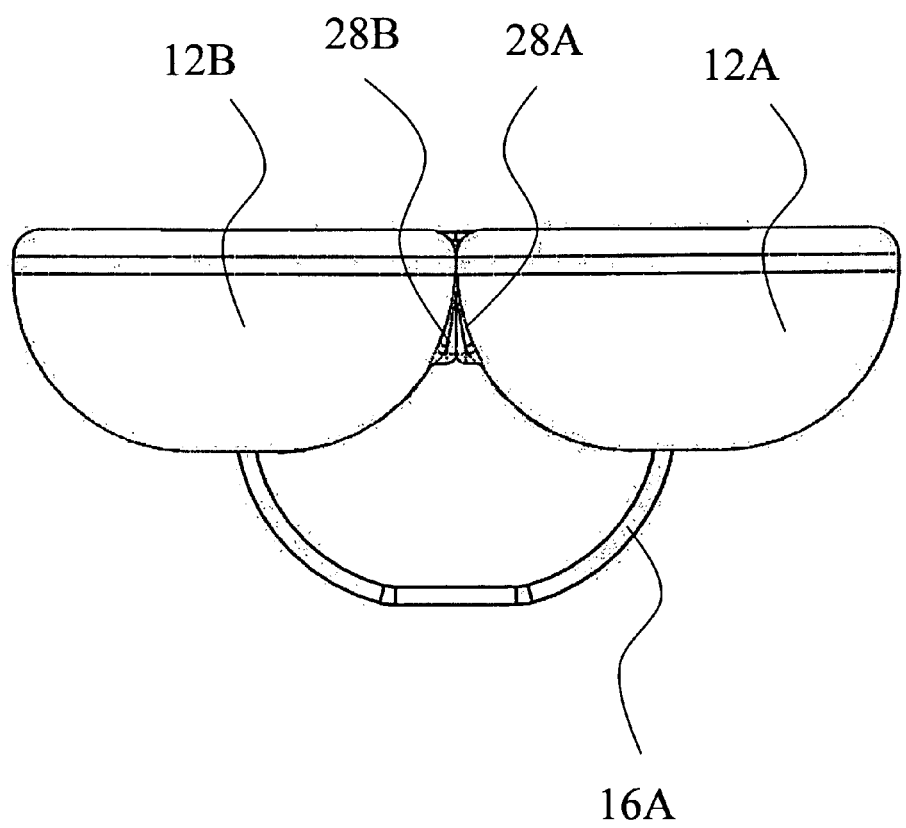
FIGS. 1C-1D are two end-on views of an open dual use compression clip and surgical port device for use inter alia in NOTES procedures, the device constructed according to the embodiment of the present invention shown in FIGS. 1A and 1B.
Figure 1D:
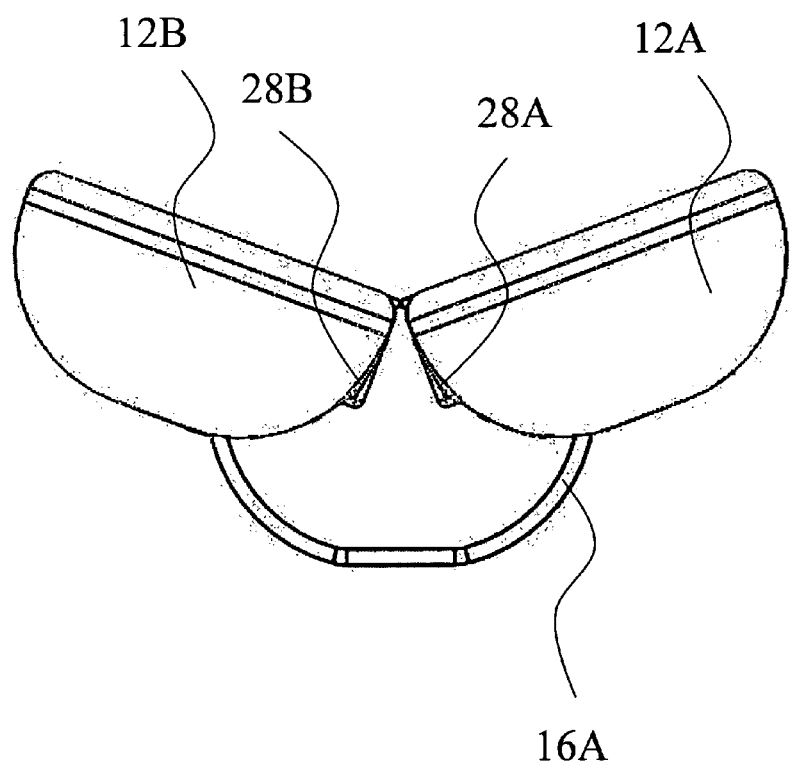
Figure 2:
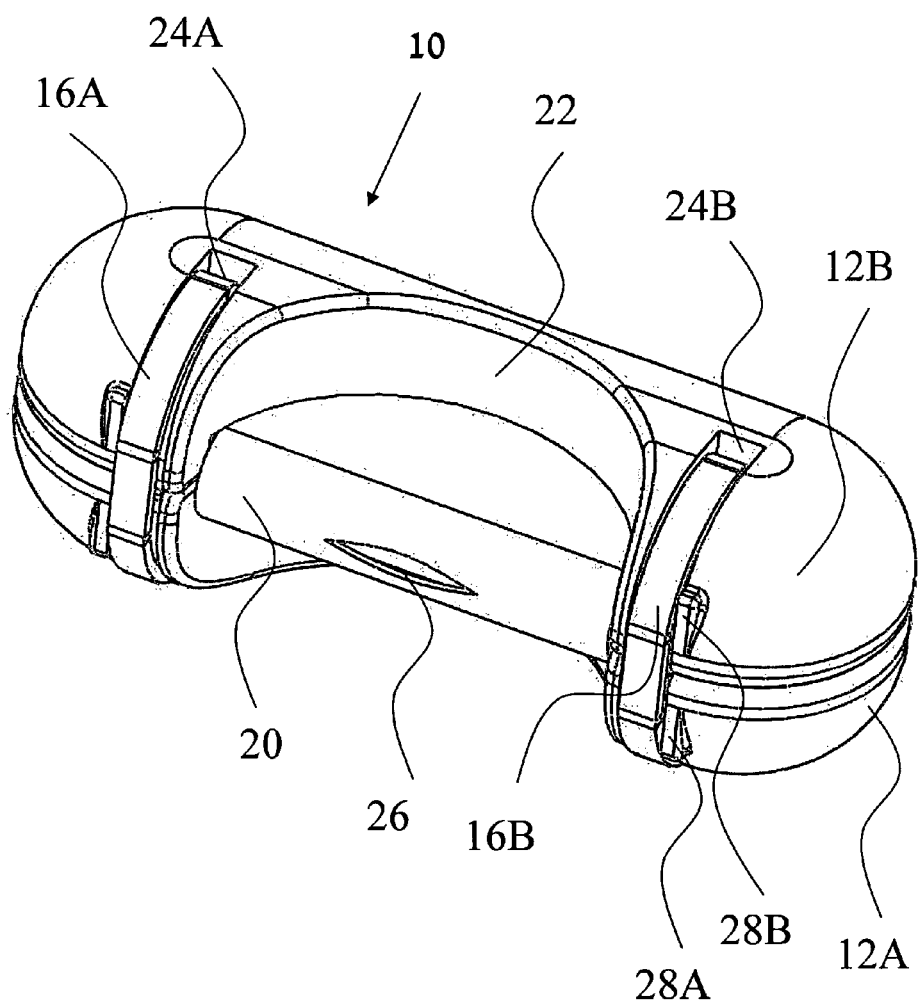
FIG. 2 is an isometric view of a closed dual use compression clip and surgical port device for use inter alia in NOTES procedures, the device constructed according to the embodiment of the present invention shown in FIGS. 1A and 1B.

FIGS. 1A and 1B, to which reference is now made, show a top side view and a bottom side view, respectively, of a dual use compression clip and surgical port device constructed in accordance with an embodiment of the present invention. The device serves as a surgical port when the device is in its open position and as a surgical compression clip when the device is in its closed position. FIGS. 1C and 1D, to which reference is also being made, show end-on views of the device in FIGS. 1A and 1B in various stages of its open port position. FIG. 2, to which reference is also being made, shows the device of FIGS. 1A and 1B in its closed configuration allowing it to function as a compression clip.

Device 10 is formed of two compression elements 12A and 12B joined at hinges 14A and 14B. Compression elements 12A and 12B may be made of plastic while hinges 14A and 14B may be made of plastic integrally molded with compression elements 12A and 12B or separately inserted to join compression elements 12A and 12B together. Hinges 14A and 14B may also be made of flexible metal insertable into compression elements 12A and 12B. The hinge elements allow pivoting of compression elements 12A and 12B bringing them close to each other so that device 10 may be brought to its closed position as in FIG. 2, thereby being capable of serving as a clip.

Compression elements 12A and 12B are constructed so that when they are in their open spaced apart arrangement they form an opening which serves as a surgical port, for example, for use in a NOTES procedure. Compression elements 12A and 12B, for example, each contain a semi-circular or arcuate edge, that is, a bounding surface 22. When compression elements 12A and 12B are held in their open arrangement their bounding surfaces together form the above mentioned surgical port.

Also shown in FIGS. 1A and 1B are applicator apertures 18, only one of which appears in the Figures, the other being obscured. These apertures are at times denoted herein as "engageable surface features". Apertures 18 serve as recesses for the insertion elements (not shown) of the arms of a force transmitting applicator instrument (not shown). The insertion elements transmit a force from the applicator instrument to device 10 causing its compression elements 12A and 12B to move from their open arrangement (FIGS. 1A-1B) to their closed arrangement (FIG. 2). Any of many suitable applicator instruments may be designed by a person skilled in the art and therefore details of such applicator instruments are not described herein. The applicator instruments may be either rigid or flexible.

As shown in FIGS. 1C and 1D there are stopper elements 28A and 28B which protrude from the surfaces of compression elements 12A and 12B. The stopper elements are intended to counter the tensile force generated by the leaf spring (see discussion below) keeping the bottom surfaces of elements 12A and 12B substantially in a plane when the device is in its open port position. This allows the device to be pressed against the inside surface of the body lumen adjacent to, or within an otherwise operational distance of, the organ undergoing the NOTES procedure. As shown in FIG. 2, stopper elements 28A and 28B are recessed in compression elements 12A and 12B when device 10 is in its closed position.

When used herein the term "otherwise operational distance" is intended to include procedures such as appendectomies where a NOTES procedure may be effected by an incision from the stomach into the peritoneal cavity. While the incision is not adjacent to the organ, the appendix, being operated on, the incision is still within a distance where the surgical procedure can be performed, that is it is within an "operational distance of the organ". An appendectomy is given by way of example only and is not intended as limiting the procedures which may be performed using the devices, systems and method of the invention.

Also present in device 10 is a membrane 20. The membrane is made of any one of several types of elastomeric materials known to persons skilled in the art, such as rubber or silicon-based elastomers. Membrane 20 may be constructed with a slit 26 in it; in FIGS. 1A-2, the slit is shown as being relatively open but in reality it is closed when device 10 is not being used as a port. The slit is self-closing as would be expected from an elastomeric material and effectively acts as a one way valve. Membrane 20 is attached to the bottom side of the opening of device 10 by any one of several possible ways known to those skilled in the art, such as gluing, ultrasonic welding or by a snap-on mechanism.

Membrane 20 keeps microorganisms of the gastrointestinal (GI) tract from entering the relatively sterile peritoneal cavity when an incision is made in the GI tract during a NOTES procedure. It also keeps gas from escaping the gastrointestinal tract when such gas is injected at the start of a NOTES procedure. Finally, as will be discussed further below, membrane 20 allows device 10 to be securely attached to the tissue being closed when staples or other anchoring elements are used to attach the device to that portion of the tissue adjacent to, or within an otherwise operational distance of, the organ undergoing the surgical procedure or to the tissue through or in which an incision is to be made.

As noted above, membrane 20 generally covers a circular opening formed by the complementary bounding surfaces 22 of compression elements 12A and 12B. In such cases the bounding surfaces are arcuate. The opening at times may be constructed to have an elliptical shape; here too the bounding surfaces would be arcuate. However, the opening need not be circular or elliptical. The compression elements can be constructed to include bounding surfaces having shapes from which a polygon-shaped port opening may be formed. In such cases, each of the bounding surfaces may be broken linear surfaces forming half the perimeter of the complete polygon-shaped surgical port.

Also joining compression elements 12A and 12B are force applier elements 16A and 16B, here leaf springs. The discussion herein will be in terms of leaf springs but it should be apparent to one skilled in the art that other force applier elements may also be used. Without intending to limit the invention, these may typically be made from a shape memory alloy such as nitinol. Force applier elements 16A and 16B are inserted into compression elements 12A and 12B at openings 24A-24D. The ends of elements 16A and 16B are biased to keep compression elements 12A and 12B in their open arrangement. However, when the applicator instrument discussed above applies a force moving the ends of force applier elements 16A and 16B in the bottom side direction past the line formed by connecting hinges 14A and 14B, the springs become biased to compress and hold elements 12A and 12B in their closed arrangement.

As noted above, force applier elements may be made of shape-memory materials, as well as other materials, such as conventional metallic spring materials, or elastomers, such as rubbers.

Applier elements having shapes other than that shown in FIGS. 1A-2 may also be used as force appliers if their function and operation are essentially similar to that of the spring and leaf spring discussed herein above.

In some embodiments of the present invention, no membrane 20 may be required While the embodiment of the present invention discussed above includes two hinge elements, in other embodiments there may be a single hinge element or more than two hinge elements.

The method for use of the above described dual use compression clip and surgical port device is outlined as follows. The description will assume that the device is being used in a typical NOTES procedure.

1. The dual use compression clip and surgical port device, typically in its open position, is brought to that portion of the inside surface of a body lumen adjacent to, or within an otherwise operational distance of, where the NOTES procedure is to take place. The device is brought through a body orifice using a rigid or flexible hollow placement means which is attached to the device. It should be understood that in other embodiments the device may be brought while in its closed configuration to the inside surface of the organ at which the NOTES is to take place and only afterward opened.
2. An endoscope transporting various working surgical instruments is advanced through the hollow placement means attached to the device and brought adjacent to the device.

3. A cutting instrument is advanced out of the distal end of the endoscope and the instrument cuts through a membrane positioned over the opening of the device and the tissue of the body lumen adjacent to the membrane.
4. A stapler is advanced out of the distal end of the endoscope and brought through the cut membrane and cut tissue to the outside of the body lumen.
5. The stapler is brought toward the tissue and membrane and both are stapled together, anchoring the device to the tissue.
6. The stapler is then retracted through the cut membrane and cut tissue and brought back into the endoscope.
7. The endoscope is advanced through the cut membrane and cut tissue to effect the procedures required on the organ positioned outside of the body lumen.
8. After completion of the required surgical procedures on the organ outside the body lumen, the endoscope is drawn inside the body lumen through the cut membrane and cut tissue.
9. An applicator instrument is activated and moves the compression elements and the ends of the force applier elements, so that they pass a virtual line formed by the two hinge elements of the device. This causes the device to move to its closed position, i.e. to bring its compression elements from their open, spaced apart, arrangement to their closed adjacent arrangement, compressing the tissue therebetween.
10. The applicator instrument is disengaged from the device and drawn into the endoscope.
11. The endoscope and other working surgical instruments are withdrawn through the hollow placement means from the body via the orifice through which they entered.
12. The dual use compression clip and surgical port device in its closed position remains attached to and compresses the tissue adjacent to the incision, thereby producing necrosis and healing. It is then naturally expelled from an orifice of the body.

In the above description of the method, a stapler and staples are used to anchor the device's membrane to the tissue around the incision area. It should readily be understood that other methods may also be used to secure the device's membrane to the tissue. These include, but are not limited to, T anchor suturing devices and other suturing devices known to those skilled in the art. The use of surgical glue devices may also be used for suturing.

Figure 3A:
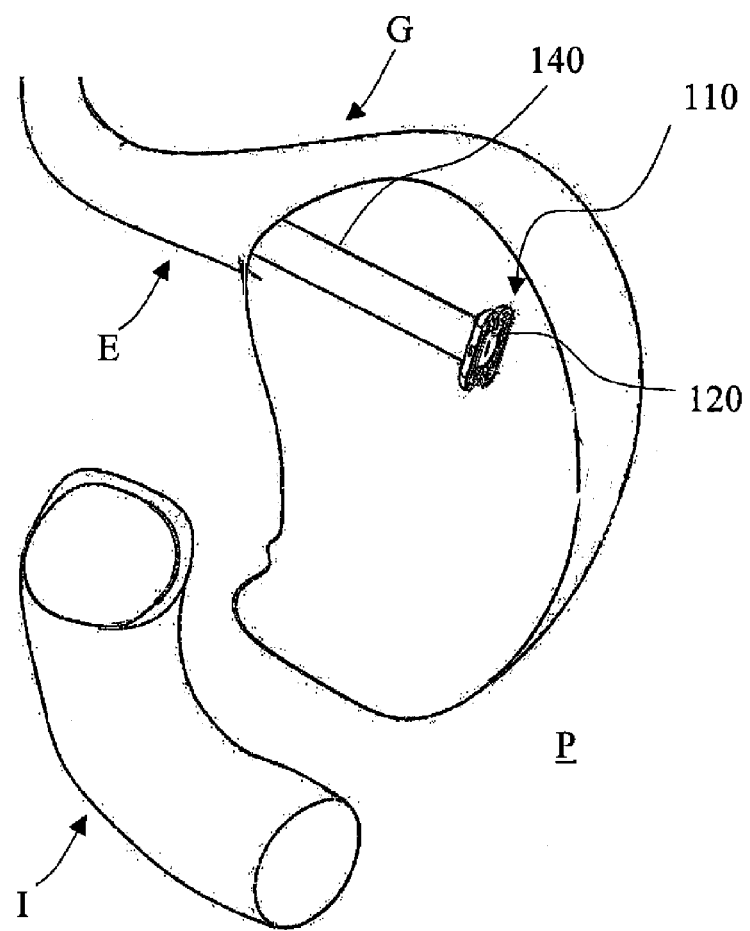
FIGS. 3A and 3B show steps in the method of applying and using the dual use compression clip and surgical port device which in its open position functions as a surgical port and in its closed position as a compression clip, the device constructed according to embodiments of the present invention.
Figure 3B:
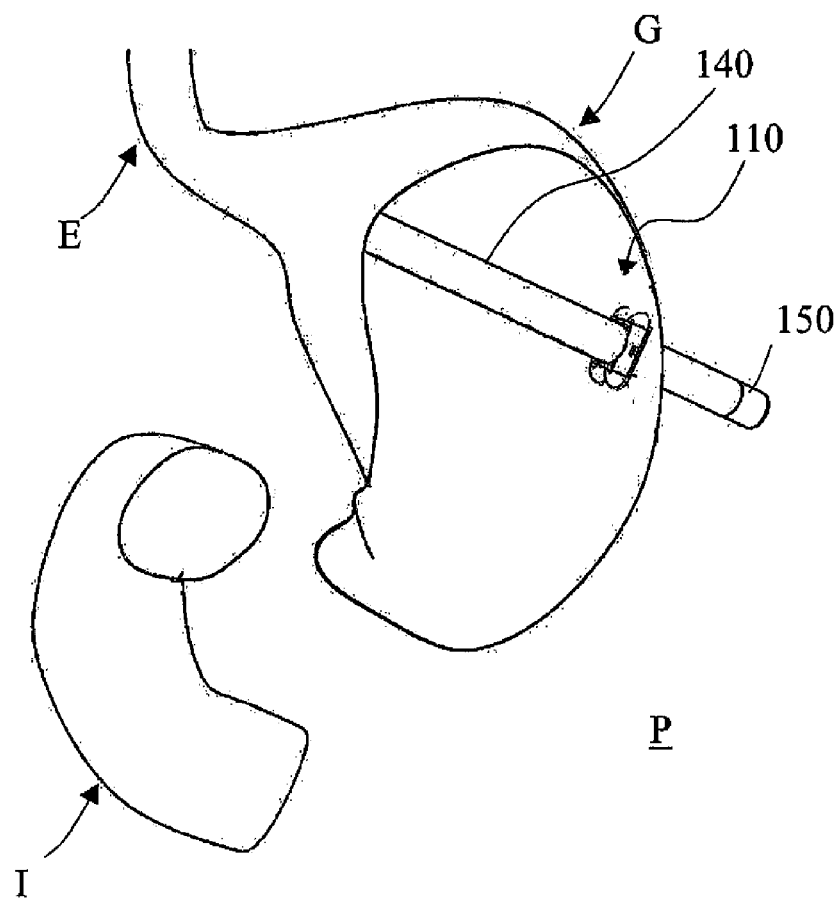

Reference is now made to FIGS. 3A and 3B which indicate two stages of the NOTES procedure described above employing the device of the present invention.

FIG. 3A shows device 110 being inserted through the esophagus E into the stomach G. A portion of the small intestine I is also shown. Attached to device 110 is a hollow placement means 140 typically formed of a polymeric plastic material. The hollow placement means may be removably attached by any of many different ways known to persons skilled in the art including but not limited to gluing and ultrasonic welding. Through hollow placement means 140, an endoscope 150 (FIG. 3B) conveying one or more working surgical instruments 155 (not shown) is also inserted. A cutting instrument conveyed through the endoscope effects an incision in the wall of stomach G. The incision (not shown) allows the endoscope to move from stomach G into the peritoneal cavity P. Hollow placement means 140 attached to device 110 ensures sterility of endoscope 150 and any cutting instrument or other working surgical instruments conveyed through the endoscope. Not shown is device 110 while it is being positioned as a port at the site of an incision.

Endoscope 150 passes through flexible perforated self-sealing membrane 120. An incision (not shown) is made in the wall of stomach G and endoscope 150 and its accompanying working surgical instruments then move into peritoneal cavity P (FIG. 3B) where any further surgical procedures needed are effected by the instruments introduced via the endoscope.

Figure 3C:
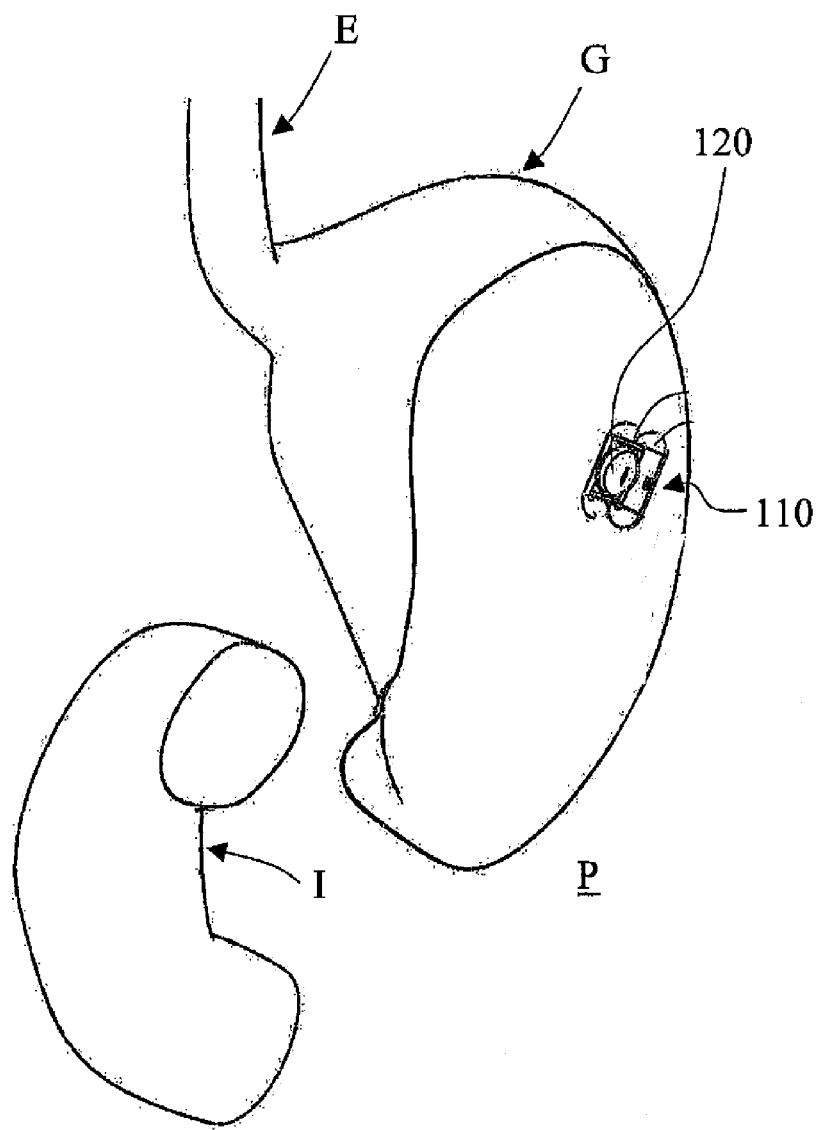
FIGS. 3C and 3D show the position of the dual use compression clip and surgical port device constructed according to embodiments of the present invention during their open port position and their closed compression position.
Figure 3D:
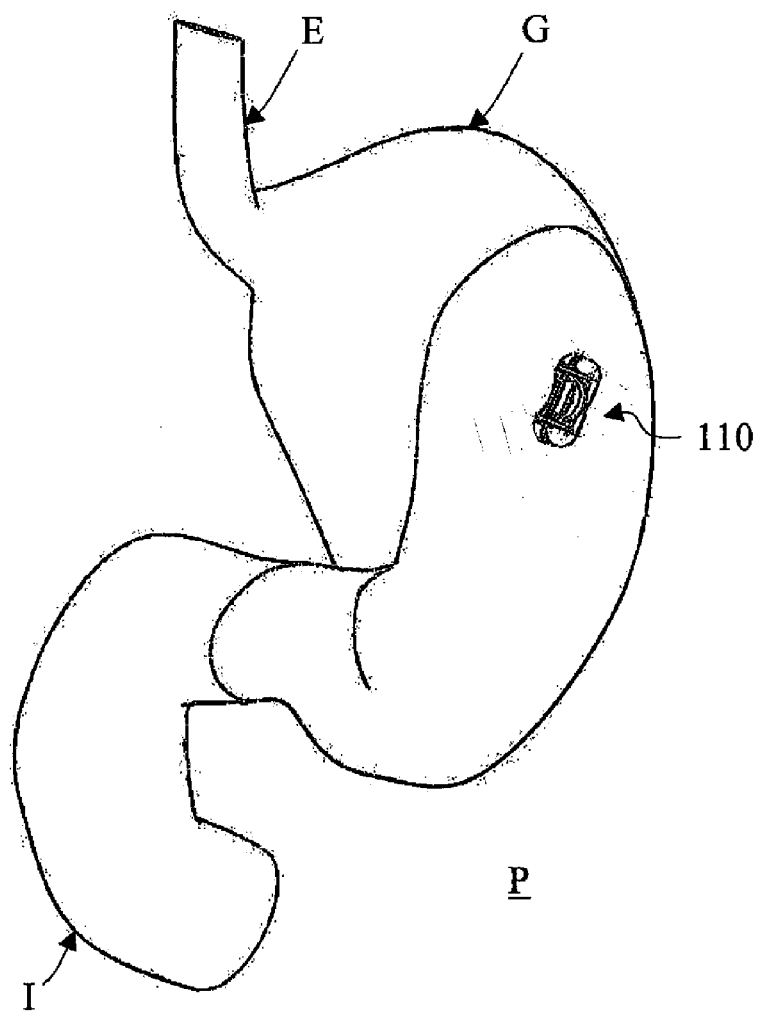

Reference is now made to FIGS. 3C and 3D. FIG. 3C shows device 110 functioning as a surgical port positioned around the point of incision prior to the incision. FIG. 3D shows device 110 compressing the incised portion of the stomach wall after removal of the endoscope and hollow placement means 140 (FIG. 3A) after completion of the surgical procedures.

Figure 4A:
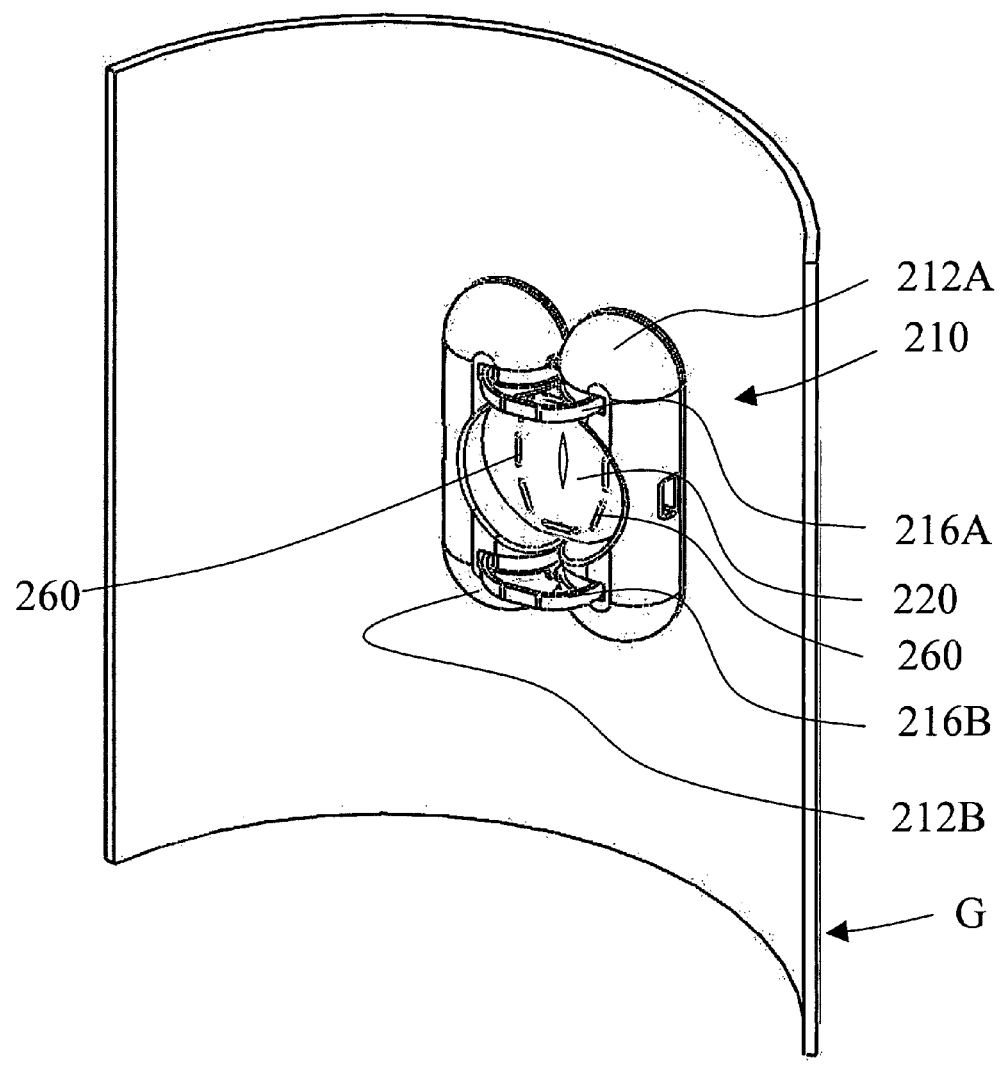
FIG. 4A shows the dual use compression clip and surgical port device positioned adjacent to the stomach wall during a NOTES procedure, the device serving as a surgical port in its open position.
Figure 4B:
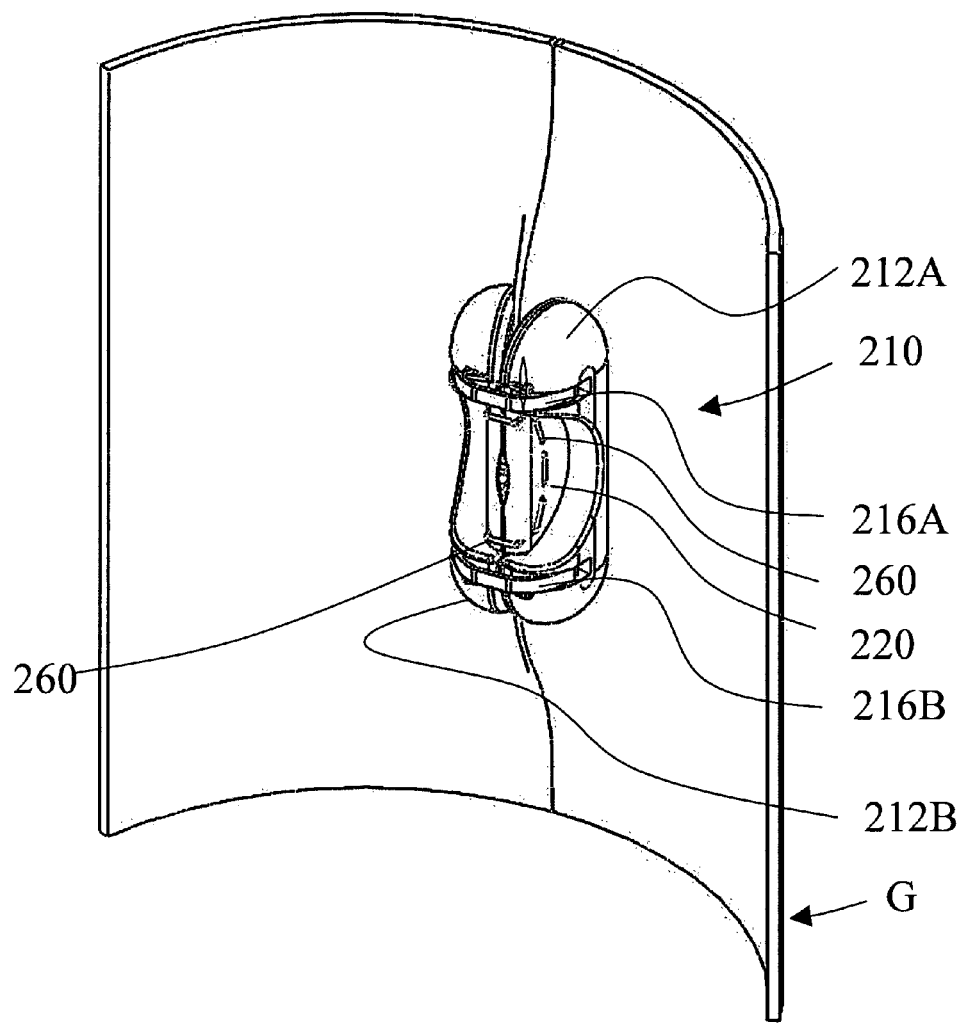
FIG. 4B shows a dual use compression clip and surgical port device in its closed position compressing the stomach wall after the completion of a NOTES procedure.
Figure 4C:
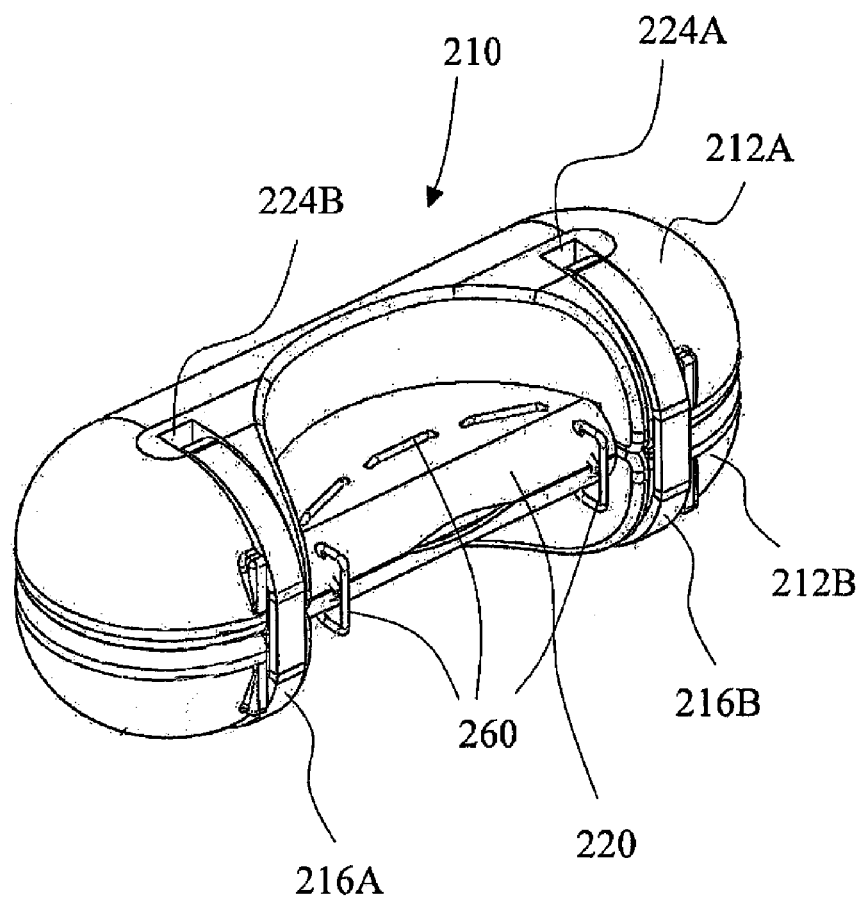
FIG. 4C shows an isometric view of the closed device.

FIGS. 4A-4C, to which reference is now made, will now be discussed. FIG. 4A shows a device 210 positioned adjacent to the region of the stomach G that has been, or will be, incised and where device 210 has functioned, or will function, as a surgical port. Anchoring of device 210 has been effected using staples introduced by a small stapler brought to the site of stapling. The stapler may be similar to an EMI 21 mm flexible circular stapler but properly sized for its intended use. Stapling is effected through both membrane 220 and the tissue of the body lumen surrounding the tissue to be incised. This fixes the port in place. The staples are shown in FIG. 4A as elements 260.

In other embodiments, a stapler need not be used. A T-anchor suturing device may be used instead. Using a series of sutures provided by the T-anchoring suturing device placed substantially symmetrically around the tissue to be incised, the tissue and the device's membrane are joined together thereby holding the device in place. In other embodiments, other suturing devices known to those skilled in the art may be used and both the membrane and the tissue around the region to be incised are sewn together allowing the NOTES procedure to proceed.

In FIG. 4B, tissue around the incised tissue is being compressed by compression elements 212A and 212B of device 210. This occurs after the endoscope and its accompanying instruments have been removed, typically but without limiting the invention, via hollow placement means 140 shown in FIGS. 3A and 3B. In FIG. 4B, the anchoring staples 260 are visible as are the remaining parts of device 210. These parts inter alia include compression elements 212A and 212B and springs 216A and 216B and membrane 220. Once necrosis and healing of the compressed tissue occurs, device 210 is evacuated via the anus after it has passed through the small and large bowels.

In FIG. 4C, there is presented a closed dual use compression clip and surgical port device 210 where compression elements 212A and 212B and force applier elements 216A and 216B, here compressing leaf springs, are shown. Applier elements (springs) 216A and 216B are attached to compression elements 212A and 212B via openings 224A and 224B formed within compression element 212A and openings 224C and 224D (obscured and not shown) formed in compression element 212B. Staples 260 hold membrane 220 and the tissue around the incised tissue together during the incision, during the surgical procedure on the organ, and during the subsequent healing process.

While what has been described herein is with respect to a NOTES procedure in the stomach, the procedure can also take place, without intending to limit the invention, in the rectum or large intestine by inserting the clip through the anus or in the uterus after insertion through the vagina.

In some embodiments of the present invention, it is contemplated that the hollow placement means as discussed above may not be required and other means may be used to properly position the device.

In another aspect of the invention, a system is envisioned. The system includes the dual use compression clip and surgical port device and an anchoring means used to anchor the device. It may also at times inter alia include a hollow placement means for bringing the device to the tissue adjacent to, or within an otherwise operational distance of, the organ undergoing the surgical procedure, an endoscope, and other working surgical instruments, for example a cutting instrument, all as described herein.

In some embodiments of the present invention, it is contemplated that the device described herein may function also as an anchoring means such as a stapler.

Figure 5A:
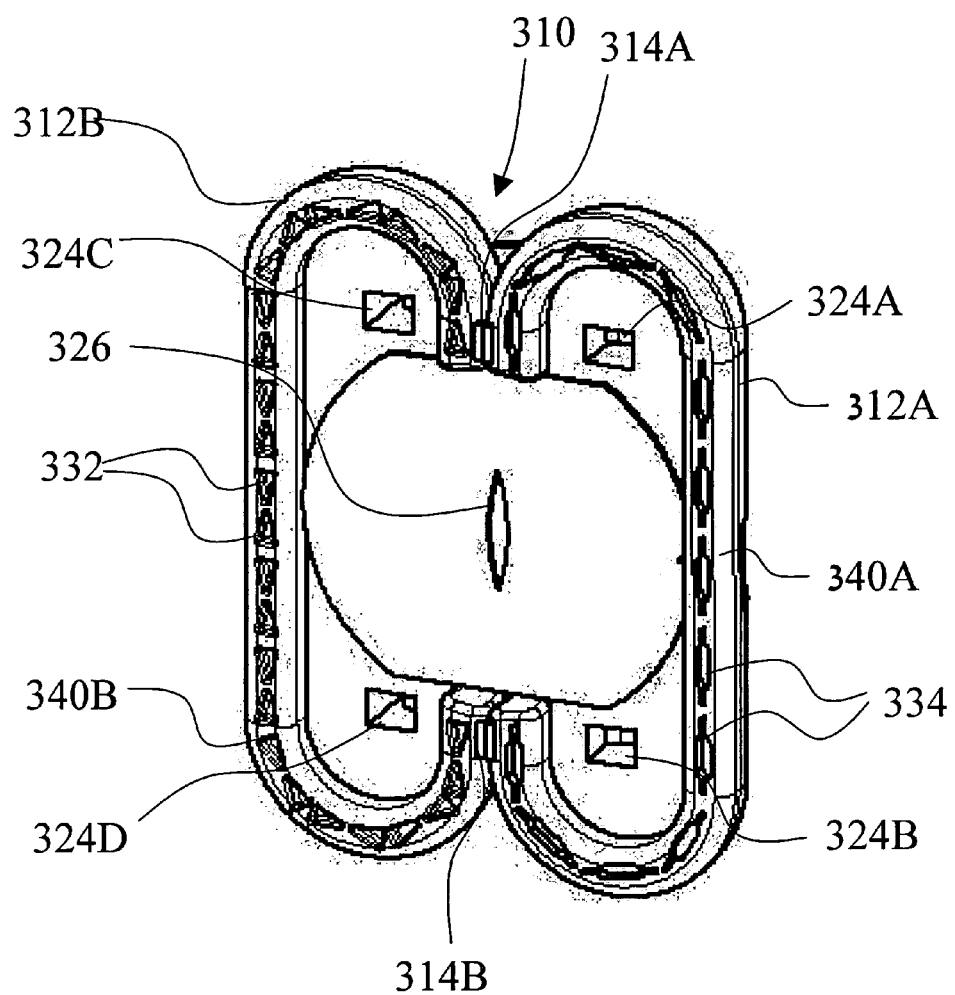
FIG. 5A is an isometric view of an open dual use compression clip and surgical port device for use inter alia in NOTES procedures, the device constructed according to another embodiment of the present invention and viewed from its bottom side.
Figure 5B:
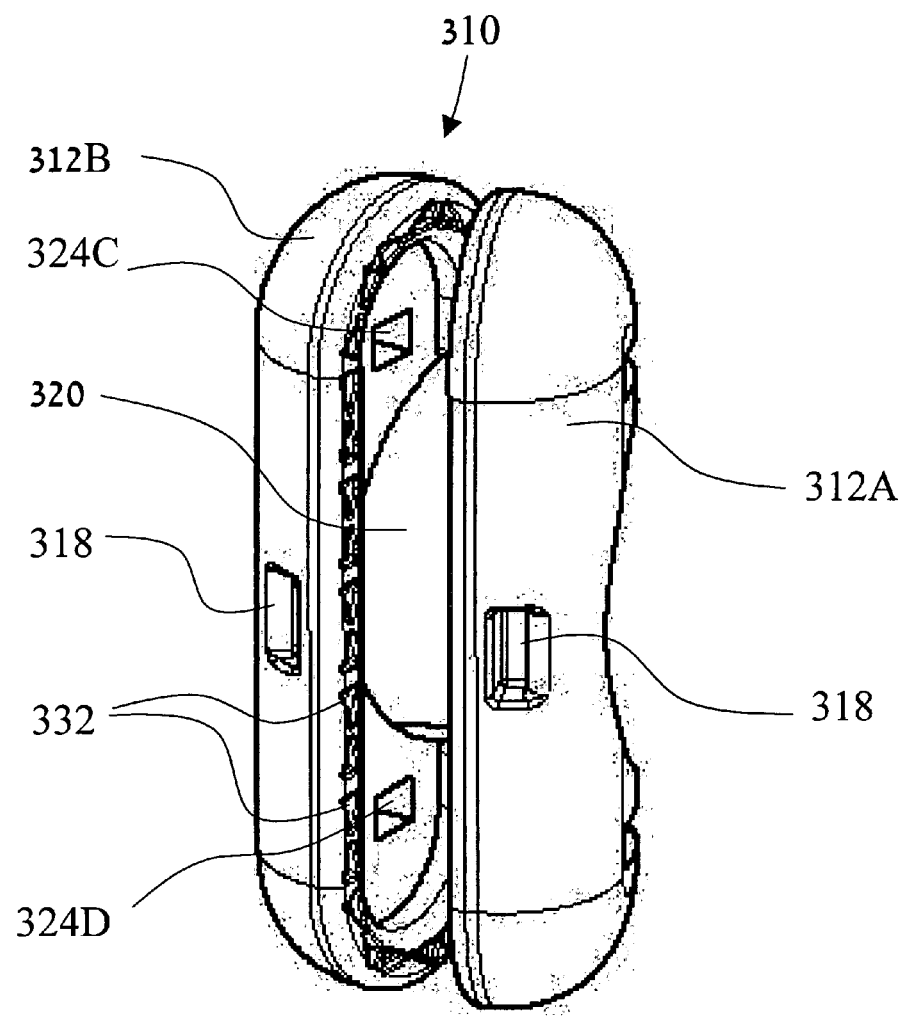
FIG. 5B is an isometric view of a closed dual use compression clip and surgical port device for use inter alia in NOTES procedures, the device constructed according to the embodiment shown in FIG. 5A.

This stapler embodiment is shown from an open bottom side view in FIG. 5A and from a closed top side view in FIG. 5B, reference to these Figures now being made. The numbering of those elements in FIGS. 5A and 5B identical to those in FIGS. 1A and 1B is the same but includes the prefix numeral "3". Since their construction and operation is the same as discussed previously, they will not be discussed again. Only features absent in FIGS. 1A and 1B will be discussed.

The lip 340A of compression element 312A of dual use compression clip and surgical port device 310 has embedded in it a plurality of staples 334 while the lip 340B of compression element 312B of device 310 includes anvil recesses 332 embedded therein. Anvil recesses 332 are in registration with staples 334. When device 310 is closed by an applicator instrument and held in its closed position by force applier elements, such as the leaf springs discussed and shown in FIGS. 1A-4C but obscured or not shown in FIGS. 5A and 5B, staples 334 are crimped after passing through the tissue compressed between compression elements 312A and 312B. The wound line produced by the incision is closed and held in place by the staples until the wound has healed.

Typical lesions which may be compressively closed using the devices, systems and method of this invention include: tissue adjacent to a disease-induced perforation of an organ wall; tissue adjacent to a perforation in the stomach wall resulting from a gastrectomy procedure; tissue adjacent to a perforation in an organ wall resulting from a natural orifice transmural endoscopic surgical (NOTES) procedure; gastric tissue adjacent to an ulcerous lesion; duodenal tissue adjacent to an ulcerous lesion; esophageal tissue adjacent to an ulcerous legion; and other tissue adjacent to an ulcerous lesion. This list is not intended to be limiting.

"Endoscope", as used herein, contemplates the use of the present invention with many different types of invasive instruments, flexible or rigid, having scope features. These include, but are not limited to, instruments referred to as endoscopes, gastroscopes, laparoscopes, colonoscopes, rectoscopes, bronchoscopes, urethroscopes, and hysteroscopes. Such instruments, as is readily known to those skilled in the art, are subsumed within the term endoscope. The present invention, while discussed in terms of general endoscopes can readily be adapted for use with each of these specific instruments with little or no modification. It should also be noted that the use of the term "endoscopic" is to be construed as referring to the many different types of invasive scopes subsumed under the term endoscopes. As known by those skilled in the art the term "invasive" denotes a medical procedure requiring insertion of an instrument or device into the body through the skin or a body orifice for diagnosis or treatment.

It should be readily apparent to one skilled in the art that the devices, systems and method of the present invention can be used on animal tissue as well as human tissue, particularly, but without being limiting, tissue of other mammalian species.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

It will be appreciated by persons skilled in the art that the present invention is not limited by the drawings and description hereinabove presented. Rather, the invention is defined solely by the claims that follow.

The invention claimed is:

1. A dual-use compression clip and surgical port device having an open and a closed position and removably attachable to an applicator instrument having insertion elements, said device comprising:

two compression elements, each element having formed thereon a bounding surface, said bounding surfaces being mutually complementary so as to combine to form the boundary of an opening when said device is in said open position;

at least one hinge element for connecting said two compression elements to each other allowing said compression elements to move from an open arrangement corresponding to said open position to a closed arrangement corresponding to said closed position and vice versa;

at least one force applier element which when said device is in said open position said at least one force applier element is biased to apply a force to keep said compression elements in said open arrangement and suitable for use as a surgical port, said at least one force applier element being selectably operable to apply to said compression elements a closure force and to maintain them in said closed arrangement when said compression elements have been brought to said closed arrangement; and at least one engageable surface feature formed on each of said compression elements and sized and configured to receive the insertion elements of the applicator instrument so that a force provided by the applicator instrument brings said compression elements from said open arrangement to said closed arrangement, thereby allowing said device to function as a compression clip when in said closed position;

wherein each of said two compression elements of said device includes a lip and wherein said lip of one of said two compression elements are embedded a plurality of staples while in said lip of said second of said two compression elements are positioned a plurality of anvil recesses, said recesses positioned to be in registration with said staples, and when said compression elements are brought to said closed arrangement and under a force produced by said at least one force applier, said staples are crimped in said recesses after passing through tissue held between said compression elements.

2. The device according to claim 1, further comprising an elastomeric membrane covering said opening of said device.

3. The device according to claim 2, wherein said membrane includes a slit for passing working tools required for a surgical procedure through said membrane.

4. The device according to claim 1, wherein said at least one force applier element is formed of a shape memory alloy.

5. A system for use as a dual use compression clip and surgical port, said system comprising:
- a dual-use compression clip and surgical port device having an open and a closed position and removably attachable to an applicator instrument having insertion elements, said device comprising:
  - two compression elements, each element having formed thereon a bounding surface, said bounding surfaces being mutually complementary so as to combine to form the boundary of an opening when said device is in said open position;
  - at least one hinge element for connecting said two compression elements to each other allowing said compression elements to move from an open arrangement corresponding to said open position to a closed arrangement corresponding to said closed position and vice versa;
  - at least one force applier element which when said device is in said open position said at least one force applier element is biased to apply a force to keep said compression elements in said open arrangement and suitable for use as a surgical port, said at least one force applier element being selectably operable to apply to said compression elements a closure force and to maintain them in said closed arrangement when said compression elements have been brought to said closed arrangement; and
  - at least one engageable surface feature formed on each of said compression elements and sized and configured to receive said insertion elements of said applicator instrument so that a force provided by said applicator instrument brings said compression elements from said open arrangement to said closed arrangement, thereby allowing said device to function as a compression clip when in said closed position;
  - wherein each of said two compression elements of said device includes a lip and wherein said lip of one of said two compression elements are embedded a plurality of staples while in said lip of said second of said two compression elements are positioned a plurality of anvil recesses, said recesses positioned to be in registration with said staples, and when said compression elements are brought to said closed arrangement and under a force produced by said at least one force applier, said staples are crimped in said recesses after passing through tissue held between said compression elements; and
  - at least one anchoring means for anchoring said device to tissue adjacent to, or within an operational distance of, an organ selected to undergo a surgical procedure.

6. The system according to claim 5, said device further comprising an elastomeric membrane covering said opening of said device.

7. The system according to claim 5, wherein said at least one force applier element is formed of a shape memory alloy.

8. The system according to claim 5, further comprising a hollow placement means removably attachable to said device for delivering said device to the tissue adjacent to, or within an operational distance of, the organ selected to undergo the surgical procedure.

9. The system according to claim 8, wherein said hollow placement means is also usable for inserting therethrough an endoscope and working surgical instruments and for delivering them to the device.

* * * * *